United States Patent
Courtney et al.

(10) Patent No.: US 9,012,868 B2
(45) Date of Patent: Apr. 21, 2015

(54) FLUORESCENCE MICROSCOPY METHODS AND APPARATUS

(75) Inventors: Patrick Courtney, Beaconsfield (GB); Alois Renn, Zurich (CH)

(73) Assignees: Perkinelmer Singapore Pte Ltd., Singapore (SG); ETH Zürich, Zürich (CH)

( * ) Notice: Subject to any disclaimer, the term of this patent is extended or adjusted under 35 U.S.C. 154(b) by 137 days.

(21) Appl. No.: 13/143,563

(22) PCT Filed: Jan. 14, 2010

(86) PCT No.: PCT/GB2010/050041
§ 371 (c)(1),
(2), (4) Date: Aug. 22, 2011

(87) PCT Pub. No.: WO2010/082048
PCT Pub. Date: Jul. 22, 2010

(65) Prior Publication Data
US 2011/0297847 A1 Dec. 8, 2011

(30) Foreign Application Priority Data
Jan. 14, 2009 (GB) .................................. 0900526.5

(51) Int. Cl.
*G01N 21/64* (2006.01)
*G02B 21/00* (2006.01)

(52) U.S. Cl.
CPC ........ *G01N 21/6458* (2013.01); *G01N 21/6428* (2013.01); *G01N 2021/6441* (2013.01); *G01N 2021/6478* (2013.01); *G02B 21/0044* (2013.01); *G02B 21/0076* (2013.01)

(58) Field of Classification Search
CPC .......... G01N 21/6428; G01N 21/6432; G01N 21/359
USPC ......... 250/459.1, 461.2, 201.3, 339.09, 252.1
See application file for complete search history.

(56) References Cited

U.S. PATENT DOCUMENTS 5,591,578 A * 1/1997 Meade et al. ................. 435/6.11
6,259,524 B1 * 7/2001 Hofstraat et al. .......... 356/243.4
(Continued)

FOREIGN PATENT DOCUMENTS

GB 2418018 3/2006

OTHER PUBLICATIONS

International Search Report and Written Opinion for corresponding International Application No. PCT/GB2010/050041, dated Oct. 1, 2010.
(Continued)

*Primary Examiner* — David Porta
*Assistant Examiner* — Djura Malevic
(74) *Attorney, Agent, or Firm* — Marshall, Gerstein & Borun LLP

(57) ABSTRACT

Methods and apparatus are provided concerning the control of photobleaching of fluorescent labels during the study of samples by fluorescence microscopy. A method is described for operating fluorescence microscopy apparatus to analyse a sample (114), the apparatus including input, processing, sample irradiating and detection arrangements (110, 112; 104; 100; 122), and the method including the steps of: receiving parameters in the processing arrangement via the input arrangement, wherein the parameters relate to an experiment to be conducted using the apparatus and include at least one parameter relating to a fluorescent label present in the sample; and determining with the processing arrangement an excitation procedure to be carried out during the experiment having regard to the inputted parameters and the rate of photobleaching of the fluorescent label desired during the experiment. Furthermore, confocal fluorescence microscopy apparatus is described which comprises an optical arrangement in the light path from an excitation energy source to a sample which acts to adjust the intensity profile of the light beam across its width so as to be more evenly distributed than a Gaussian profile and/or includes a spinning disk, wherein the rotational speed of the disk is variable under the control of a processing arrangement of the apparatus.

22 Claims, 13 Drawing Sheets

(56) References Cited

U.S. PATENT DOCUMENTS

| | | | |
|---|---|---|---|
| 6,388,746 B1* | 5/2002 | Eriksson et al. | 356/318 |
| 6,772,070 B2* | 8/2004 | Gilmanshin et al. | 702/19 |
| 6,991,939 B2* | 1/2006 | Walt et al. | 436/172 |
| 7,342,219 B2* | 3/2008 | Araya et al. | 250/234 |
| 2003/0071226 A1 | 4/2003 | Engelhardt | |
| 2003/0151742 A1* | 8/2003 | Silvermintz et al. | 356/318 |
| 2006/0050375 A1 | 3/2006 | Mikuriya et al. | |
| 2006/0073483 A1* | 4/2006 | White et al. | 435/6 |
| 2006/0087727 A1 | 4/2006 | Brooker | |
| 2007/0201130 A1* | 8/2007 | Fujinoki et al. | 359/398 |
| 2010/0003765 A1* | 1/2010 | Dixon et al. | 436/172 |
| 2010/0053743 A1* | 3/2010 | Galimberti et al. | 359/385 |

OTHER PUBLICATIONS

Hoebe et al., Controlled light-exposure microscopy reduces photobleaching and phototoxicity in fluorescence live-cell imaging, Nat. Biotechnol., 25:249-53 (2007).

Poher et al., Optical sectioning microscopes with no moving parts using a micro-stripe array light emitting diode, Opt. Express, 15:11196-206 (2007).

Shaner et al., A guide to choosing fluorescent proteins, Nat. Methods, 2:905-9 (2005).

Rasnik et al., Nonblinking and long-lasting single-molecule fluorescence imaging, Nat. Methods, 3:891-3 (2006).

Betzig et al., Imaging intracellular fluorescent proteins at nanometer resolution, Science, 313:1642-5 (2006).

Rust et al., Sub-diffraction-limit imaging by stochastic optical reconstruction microscopy (STORM), Nat. Methods, 3:793-5 (2006).

Donnert et al., Macromolecular-scale resolution in biological fluorescence microscopy, PNAS, 103:11440-5 (2006).

Donnert et al., Major signal increase in fluorescence microscopy through dark-state relaxation, Nat. Methods, 4:81-6 (2007).

Hagen et al., Biological applications of an LCoS-based programmable array microscope (PAM), Proc. SPIE, 6441, 64410S (2007).

* cited by examiner

FLUORESCENCE MICROSCOPY METHODS AND APPARATUS

FIELD OF THE INVENTION

The present invention relates to methods and apparatus for use in fluorescence microscopy. More particularly it is concerned with the control of photobleaching of fluorescent labels during the study of material samples by means of fluorescence microscopy.

BACKGROUND TO THE INVENTION

In the study of biological and biochemical samples, fluorescent labels are often used as markers for species of interest. The fluorescent label is typically a small molecule with ring structures or a genetically encoded fluorescent protein, although in some cases the intrinsic fluorescence of a species already present in the sample may be used as the fluorescent label. These labels are detected by means of photons emitted when the labels relax from an excited state to a ground state. A process of repeated excitation-emission tends to result in "photobleaching" whereby the labels lose their ability to fluoresce and may produce a species damaging to the sample under study.

The process of photobleaching is thought to involve transition of photons into a bleached state via a dark (or triplet) state. It appears that this dark state is long-lived and is susceptible to bleaching, as illustrated in FIG. 1. Different fluorescent labels exhibit different emission and bleach profiles. Increasing the bleaching rate reduces the ability to image a sample over long periods of time, particularly when using a relatively noisy detection system.

Scientists studying biological systems are interested in observing samples over periods of time and with enough spatial and temporal resolution to distinguish events of interest. These requirements place considerable demands on the performance of the fluorescent labels and in particular their resistance to photobleaching under an often intense excitation beam. The bleaching rate is therefore often a significant factor in the selection of a suitable fluorescent label.

Fluorescence microscopy may image a sample using a wide-field format. Alternatively, a confocal imaging system may be used, in which an arrangement of optics and matching pinholes restrict the light so as to focus on a particular plane. A common implementation is the "Laser Scanning Confocal Microscope" (LSCM). In this design, a single intense beam of light is scanned across a sample and the resulting fluorescence detected using a photomultiplier tube. These systems expose the sample, and thus the fluorescent labels, to very intense light for short periods of time in order to scan the entire field of view. For example, an exposure time of 4 microseconds may be used in order to obtain a 500×500 pixel image in one second. This often results in rapid photobleaching of the fluorescent labels.

An alternative approach is to scan the sample with a slit rather than a pinhole. This allows more light to be used to illuminate the sample at the cost of reduced confocal sectioning ability.

A further approach is to apply a scanning protocol to scan a number of pinholes in parallel to create an image on an array detector such as a CCD. This may be achieved using a spinning disk, whereby one or more perforated disks are rotated between the excitation light source and the sample, such that each point on the same receives a brief burst of light as the disk(s) rotate, with many distinct points excited at any one time. Alternatively, the pinhole may be scanned in the x and y directions to build up an image.

In a related approach, a set of pinholes is created and scanned using a controllable array of optical elements to synthesise an array of pinholes. This approach is sometimes called "Programmable Array Microscopy" (PAM). Each element is under computer control and may be switched to emulate the pinhole disc without any large moving parts [Hagen 2007].

For example when the optical element is a controllable mirror switchable to an angle of 0 degrees or 10 degrees (such as in the Texas instruments Digital Micro-mirror Device), the optical path is arranged so that the light from the excitation source passes to the array and may be reflected onto the sample at each point when the mirror is switched on, or away from the sample when the mirror is switched off. Similarly, the optical element may be a controllable light cell switchable to be transparent or dark (such as in a spatial light modulator), and the optical path is arranged so that the light from the excitation source passes through the array before reaching the sample at each point when the light cell is switched on, or not reaching the sample when the light cell is switched off.

Another technique for scanning a sample with excitation light involves provision of an array of individual light sources such as light emitting diodes (LEDs). Each element is under computer control and may be switched to emulate the pinhole disc without any moving parts [Poher 2007].

The presence of molecular oxygen in a sample has been found to increase the rate at which bleaching takes place. One approach designed to reduce this bleaching is to purge the oxygen with another gas such as nitrogen. This has been found to be applicable to simply biochemical systems such as samples spin-coated on slides.

Alternatively, the use of a chemical oxygen scavenger system has been suggested, for example an enzymatic system of glucose oxidase and catalase. This may be supplemented with a triplet-state quencher [Rasnik 2006]. This is suitable for cell-free systems, but in many samples, the oxygen plays an important role and so it may not be possible to remove it without interfering with the processes of interest.

Another proposal for reducing photobleaching is to reduce the light dose received by the sample by modulating the excitation according to the detected signal. This is on the basis that the brightest regions need less excitation, and dark areas do not need to be exposed. This has been referred to as "Controlled Light Exposure Microscopy" (CLEM) [Hoebe 2007].

In many fluorescence microscopes, an illumination option is available in which a dye of interest is bleached intentionally. This provides a means of studying mobility rate, bound fractions, binding rates and so on using a set of related techniques often referred to as "Fluorescence Recovery After Photobleaching" (FRAP). The aim is to bleach the dye as effectively as possible. This may be achieved by imaging the sample at an increased light intensity which eventually bleaches the dye.

In another technique, the ability to accurately localise molecules labelled with a fluorescent dye may be estimated using numerically fitting techniques to process signals representing detected radiation. By selective bleaching a certain proportion of the labels, the chance of detecting isolated fluorescent dye molecules is enhanced. Accumulating sets of images with different subsets of bleached and unbleached molecules allows a form of ultra-high resolution to be completed with considerably improved resolving power relative to that available using bulk imaging of all dye molecules. Two such schemes have been published: "Photo-activated Localisation Microscopy" (PALM) [Betzig 2006] and "Sub-Defraction-Limit Imaging By Stochastic Optical Reconstruction Microscopy" (STORM) [Rust 2006]. These techniques are assisted by the use of photo-activation or transient photobleaching which allow different subsets of molecules to be detected and localised in each group of images in multiple cycles of imaging and selective bleaching.

SUMMARY OF THE INVENTION

The present invention provides a method of operating fluorescence microscopy apparatus to analyse a sample, the apparatus including input, processing, sample irradiating and detection arrangements, the method comprising the steps of:
  (a) receiving parameters in the processing arrangement via the input arrangement, wherein the parameters relate to an experiment to be conducted using the apparatus and include at least one parameter relating to a fluorescent label present in the sample;
  (b) determining with the processing arrangement an excitation procedure to be carried out during the experiment having regard to the inputted parameters and the rate of photobleaching of the fluorescent label desired during the experiment;
  (c) irradiating at least part of the sample with the sample irradiating arrangement in accordance with the excitation procedure; and
  (d) detecting with the detection arrangement fluorescent radiation emitted by the labels in the sample in response to the excitation energy.

Accordingly, the excitation procedure may be controlled so that, in some embodiments, it maximises the emission and therefore the information provided by a given type of fluorescent label, whilst reducing or minimising the rate at which the label becomes photobleached. This is achieved by setting the parameters of the excitation procedure or regime (such as excitation pulse duration, power level, and pulse repetition rate) so that they increase, and in some cases, maximise, the total photon emission. The procedure is determined with a view to increasing the overall emission rate at which the fluorescent labels can relax from their excited state to their ground state for a given experiment and experimental conditions, whilst reducing the rate at which the fluorescent labels can move from the dark (or triplet) state to the bleached state. The specific characteristics of the fluorescent labels present in the sample are taken into account in devising the experimental procedure.

Conversely, the excitation procedure may be controlled so that it increases or maximises the rate at which the fluorescent labels become photobleached. This is achieved by setting the parameters of the excitation procedure or regime to cause an increase in the total photon emission by decreasing the overall rate at which the fluorescent labels can relax from excited to ground state for a given experiment and experimental conditions, whilst increasing the rate at which the fluorescent labels will move from the dark (or triplet) state to the bleached state.

Controlling and reducing the rate of photobleaching allows the study of samples for longer periods of time and/or with a greater temporal sampling rate, whilst reducing the risk of damage or perturbation. The total number of photons emitted may be increased, thereby enhancing the ability of the apparatus to reveal information about the system under study. In accordance with approaches described herein, the bleaching effect may be adjusted or optimised according to the specifics of a given experiment.

In addition, some fluorescent labels have attractive properties, for example associated with their excitation or emission spectra, or because they are relatively insensitive to interfering species, but are currently unsuitable for use due to their sensitivity to photobleaching. Examples include HcRED-tandem, mBanana, mHoneydew, mRaspberry, mRFP1, mTangerine, and PhiYFP [Shaner 2005]. Techniques described herein may make use of these and other fluorescent labels that are particularly sensitive to photobleaching much more feasible.

The relationship between bleaching and excitation parameters for a given fluorescent label may be explored using test samples and a set of test excitation regimes, or by using a pre-established library of data. This information can then be employed by the processing arrangement in the determination of an appropriate excitation regime, having regard to parameters of the experiment such as the desired imaging rate, and the experiment duration.

The input parameters may include at least one of: the excitation procedure duration, the sampling rate of the detection arrangement, the location and dimensions of a part of the sample to be irradiated, the relative speed of a process of interest in the sample, the rate at which a beam of irradiation energy is scanned over the sample, and the intensity of the excitation energy. They may include at least one of the following sample parameters: temperature, the concentration of a fluorescent label in the sample, oxygen concentration, the presence of an oxygen scavenger system, and a parameter relating to an oxygen scavenger system present in the sample.

The input parameters may include at least one of the following fluorescent label parameters: peak excitation wavelength, peak emission wavelength, fluorescence lifetime, triplet state decay lifetime, and a parameter identifying a particular fluorescent label.

The excitation procedure may be determined by the processing arrangement in step (b) having regard to at least one of the following characteristics of the apparatus: the level of detector background noise, the maximum power output of the sample irradiating arrangement, the capabilities of a shutter arrangement associated with a source of irradiation energy, and the capabilities of a sample scanning mechanism. In particular, it may be determined by the processing arrangement in step (b) having regard to the rotational speed of a spinning disk in the sample scanning mechanism.

Preferably, the processing arrangement determines at least one of the following aspects of the excitation procedure in step (b): the excitation pulse duration, the pulse intensity versus time profile, the pulse repetition rate, the time interval between groups of pulses, and the rotational speed of a spinning disk in a sample scanning mechanism.

The sample irradiating arrangement is operable to vary the power of a beam of excitation energy generated during an excitation pulse so as to control the pulse intensity versus time profile.

In some embodiments, the sample includes a plurality of different fluorescent labels, and the processing arrangement determines a respective excitation procedure to be carried out during the experiment for at least two different fluorescent labels.

The excitation procedure may be determined by the processing arrangement in step (b) having regard to an electronically accessible library of test data relating to the fluorescence characteristics of a plurality of fluorescent labels.

According to another aspect of the invention fluorescence microscopy apparatus is provided which comprises:
  (i) an input arrangement for inputting parameters relating to an experiment to be conducted, which parameters include at least one parameter relating to a fluorescent label present in the sample;

(ii) a processing arrangement for determining an excitation procedure to be carried out during the experiment having regard to the inputted parameters and the degree to which photobleaching of emissions from the fluorescent label is desired during the experiment;

(iii) a sample irradiating arrangement for irradiating at least part of the sample in accordance with the excitation procedure; and (iv) a detection arrangement for detecting fluorescent radiation emitted by labels in the sample in response to the excitation energy.

In preferred embodiments, an optical arrangement is provided in the light path from an excitation energy source to a sample which acts to adjust the intensity profile of the light beam across its width so as to be more evenly distributed than a Gaussian profile.

A further aspect of the invention provides confocal fluorescence microscopy apparatus comprising an optical arrangement in the light path from an excitation energy source to a sample which acts to adjust the intensity profile of the light beam across its width so as to be more evenly distributed than a Gaussian profile. Modulation of the beam profile so that its intensity is more evenly distributed or "flatter" can reduce the rate of bleaching. The optical arrangement may comprise a Fresnel lens.

Confocal fluorescence apparatus may be provided according to one embodiment which includes a spinning disk having an array of microlenses therein, each of which acts to adjust the intensity profile of the respective light beam across its width so as to be more evenly distributed than a Gaussian profile.

Another aspect of the present invention provides confocal fluorescence microscopy apparatus including a spinning disk, wherein the rotational speed of the disk is variable under the control of a processing arrangement of the apparatus. The rotational speed may therefore be controlled according to the objectives of the experiment and the characteristics of the sample under study. This may also enable the intensity and relaxation time operating points to be set for two or more different types of label in a given sample and allow rapid switching between them as each label is imaged, for example between successive frames as excitation and/or emission filters are changed.

Embodiments of the invention in the form of confocal fluorescence microscopy apparatus may include a multiple point scanning mechanism having a mask arrangement which defines at least two regions having different respective aperture configurations, the apparatus being configured to select one of the regions for use in a particular excitation procedure.

More particularly, the mask arrangement may comprise one of: a spinning disk, a linear band, and a translating array. The at least two regions may differ with respect to at least one of: the dimensions of the apertures, and the spacing between the apertures.

BRIEF DESCRIPTION OF THE DRAWINGS

The prior art and embodiments of the invention will now be described by way of example and with reference to the accompanying schematic drawings, wherein.

DETAILED DESCRIPTION OF THE DRAWINGS

Development of the techniques described herein involved consideration of the relationship between the total number of photons emitted by a fluorescent label as a function of intensity, the inter-pulse relaxation time, and both these parameters together.

Figure 1:
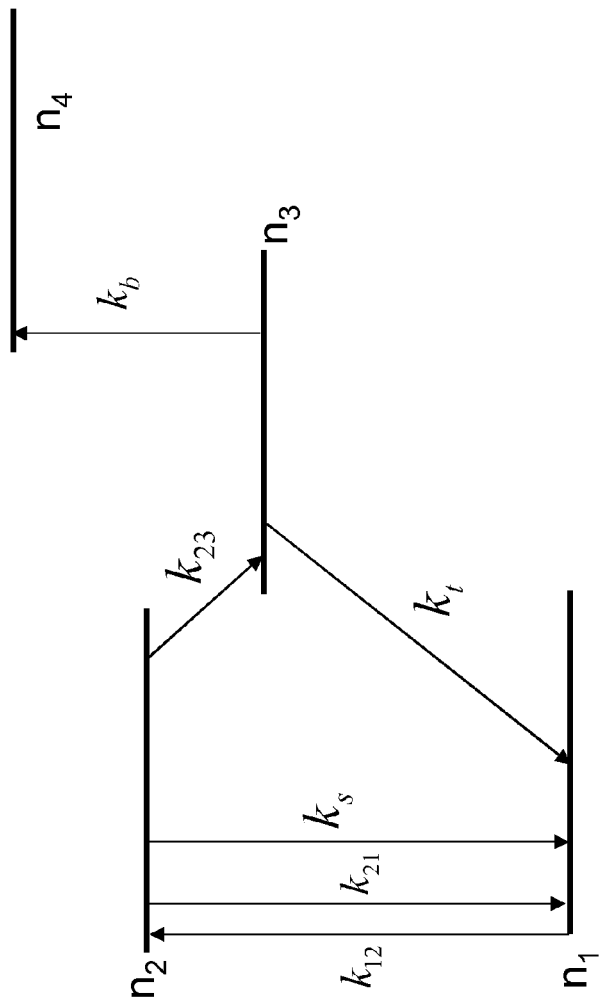
FIG. 1 represents a four-level model of energy states for fluorescent molecules.
Figure 2:
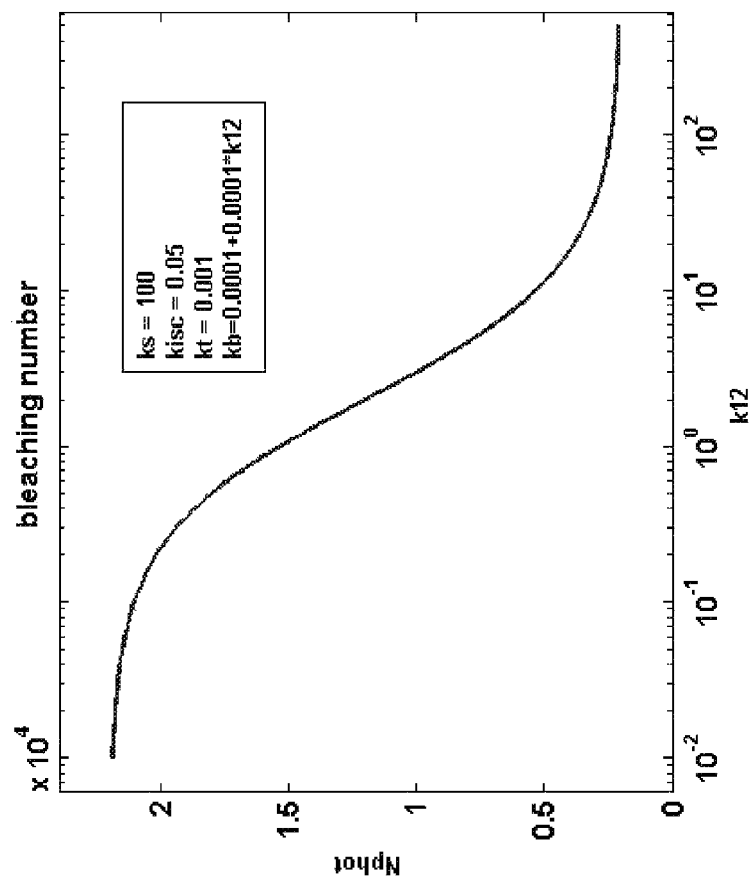
FIG. 2 is a plot of the total number of photons emitted against relative intensity generated using the model of FIG. 1.

A four-level theoretical model was developed to represent the photobleaching mechanism as shown in FIG. 1. Increasing the overall light intensity is simulated by changing the values of K12 and Kb, the photon-induced excitation from the ground state ($n_1$) to an excited stated ($n_2$) and from the triplet state ($n_3$) to a bleached state ($n_4$), respectively. K12 alone does not change the total number of photons emitted. However, a complete set of simulations for varying Kb (FIG. 2) reveals three regions of interest. At higher levels of excitation intensity, the total number of photons emitted (Nphot) tends towards a relatively low value, as a result of photobleaching. Over a middle region of excitation intensity, the total number of photons emitted increases and the bleach rate decreases with decreasing excitation intensity (that is, decreasing magnitude of the parameter K12). At lower levels of excitation energy the total number of photons emitted tends towards a relatively high value as the excitation intensity decreases.

The model shown in FIG. 1 indicates that the rate at which dye molecules are bleached will depend on two primary factors: (i) the population of molecules in the triplet state and (ii) the rate at which dye molecules are excited from this state. The former is a function of excitation intensity, whilst the latter is also a function of excitation intensity. As a consequence, the bleach rate can be seen to depend on the square of the excitation intensity. Therefore, reducing the excitation intensity will give disproportionately more photons and information about the system under study, providing that the longer exposure times are compatible with other parameters of the experiment and assuming that there are no other bleaching mechanisms operating.

Figure 3:
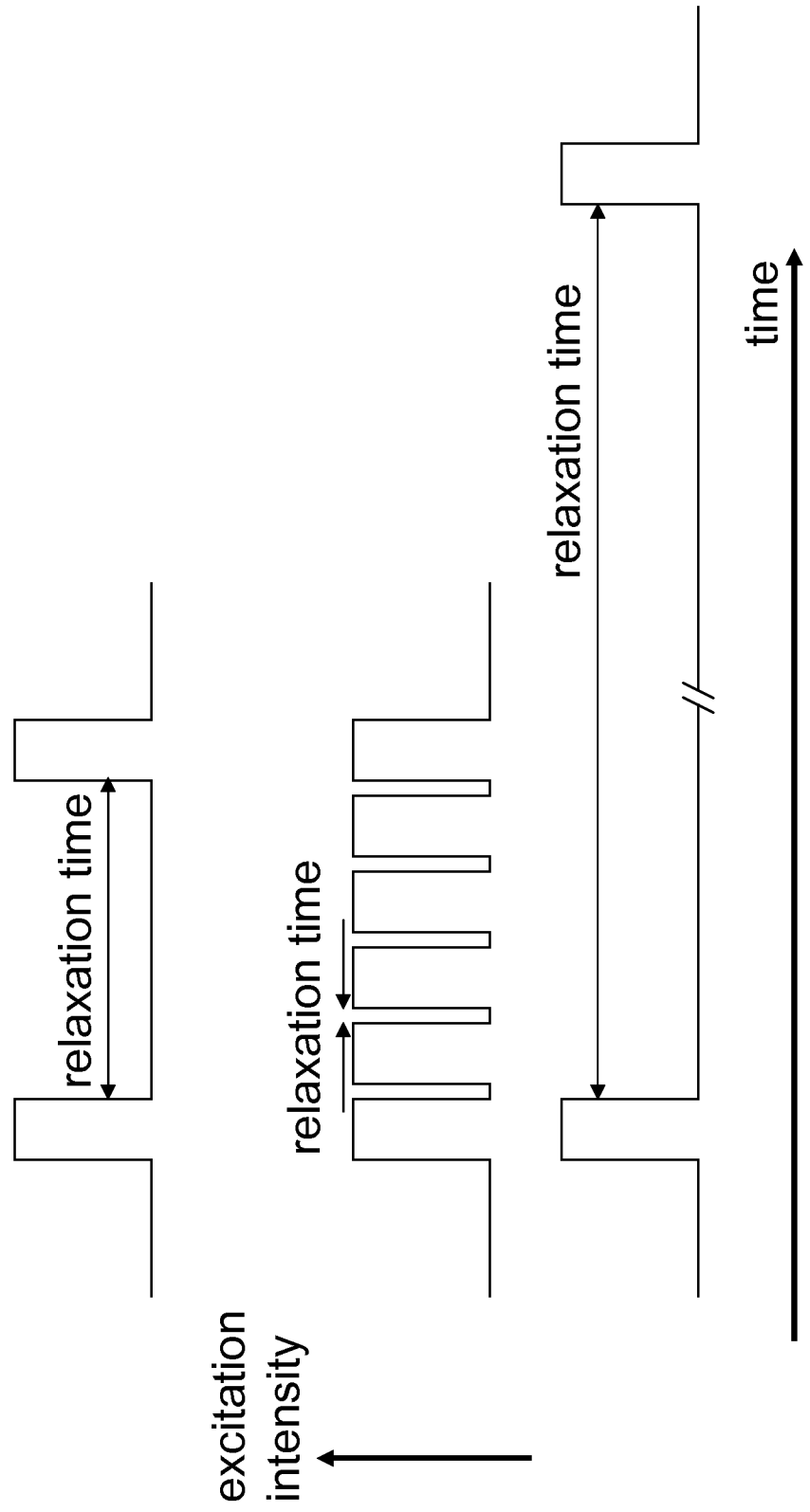
FIG. 3 illustrates three different pulsed excitation regimes.

In a pulsed excitation regime with a short on-time and a longer off-time, molecules in the triplet state tend to relax back to the ground state during the off-time, which may reduce the rate of photobleaching. FIG. 3 shows a number of possible excitation regimes having different relaxation times.

Figure 4:
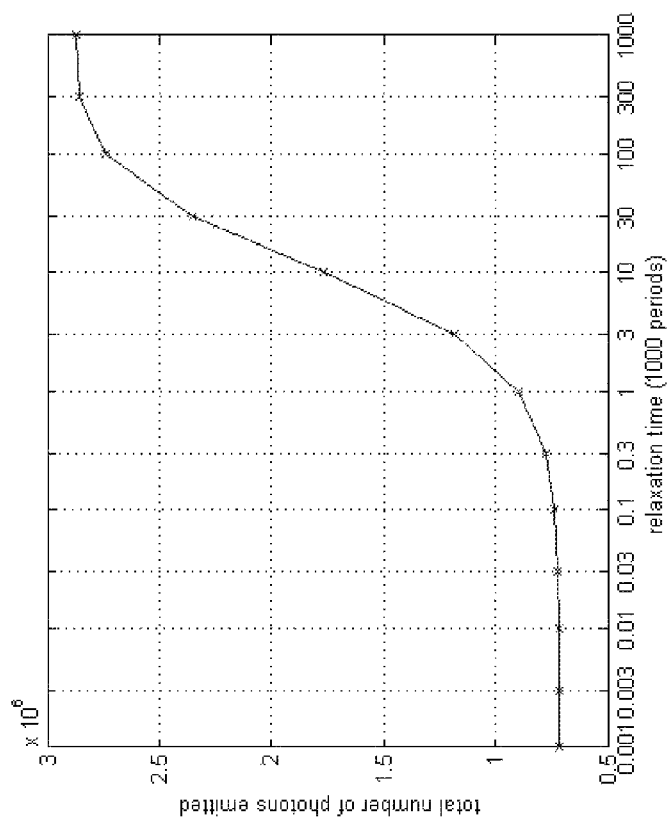
FIG. 4 is a plot of the total number of photons emitted against relaxation time generated using the model of FIG. 1.

Computer simulation using the four-level model of FIG. 1 for pulsed excitation reveals a non-linear dependence between the off-time (relaxation time) and the total number of photons emitted for a fixed number of excitation pulses (see FIG. 4).

At short relaxation times, the total number of photons emitted is fixed. With increasing relaxation time, the total number of photons increases gradually as the molecules in the triplet state have time to relax. This gain is however limited, and beyond a certain point the curve flattens off again. The location of the points of inflection depends on the values of the constants Kb, Kt and K12 used, which vary depending on the dye molecule employed and the experimental conditions. Increasing the relaxation time will therefore give more photons and thus more information about the system under study.

Figure 5:
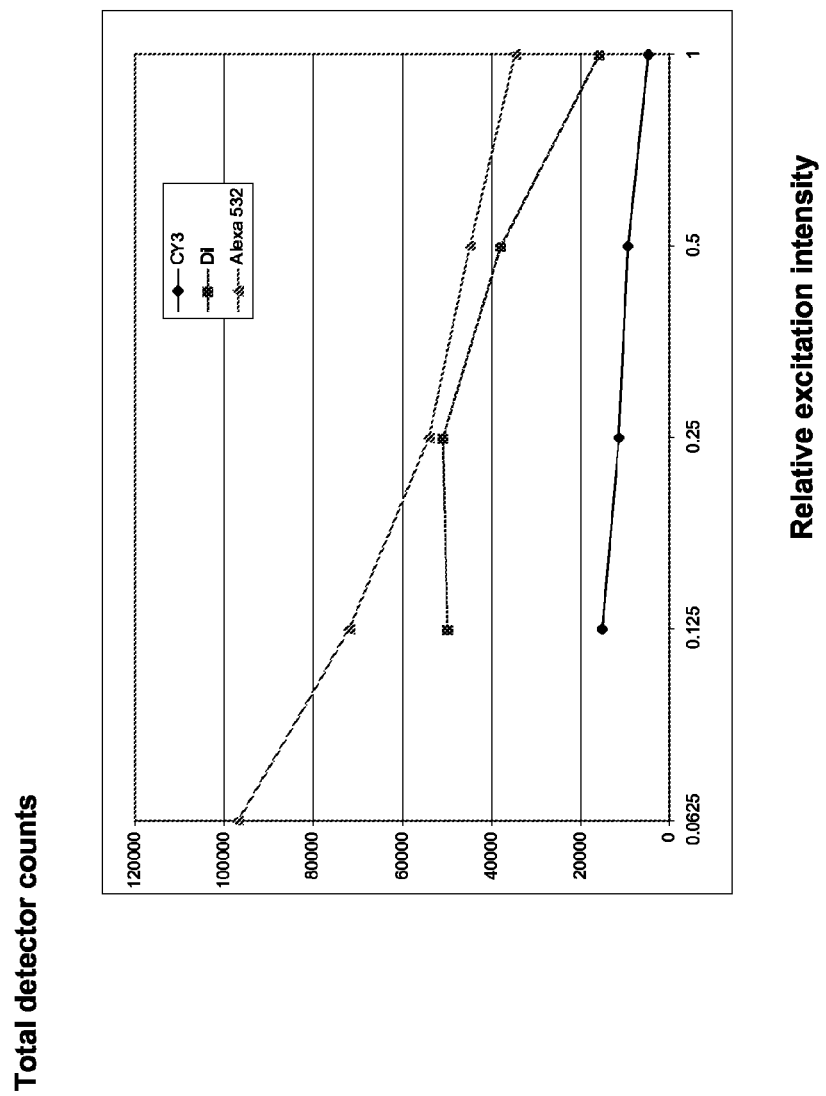
FIGS. 5 and 6 are plots of experimental data for a number of fluorescent dyes, plotting fluorescence emission against relative excitation intensity and relaxation time, respectively.
Figure 6:
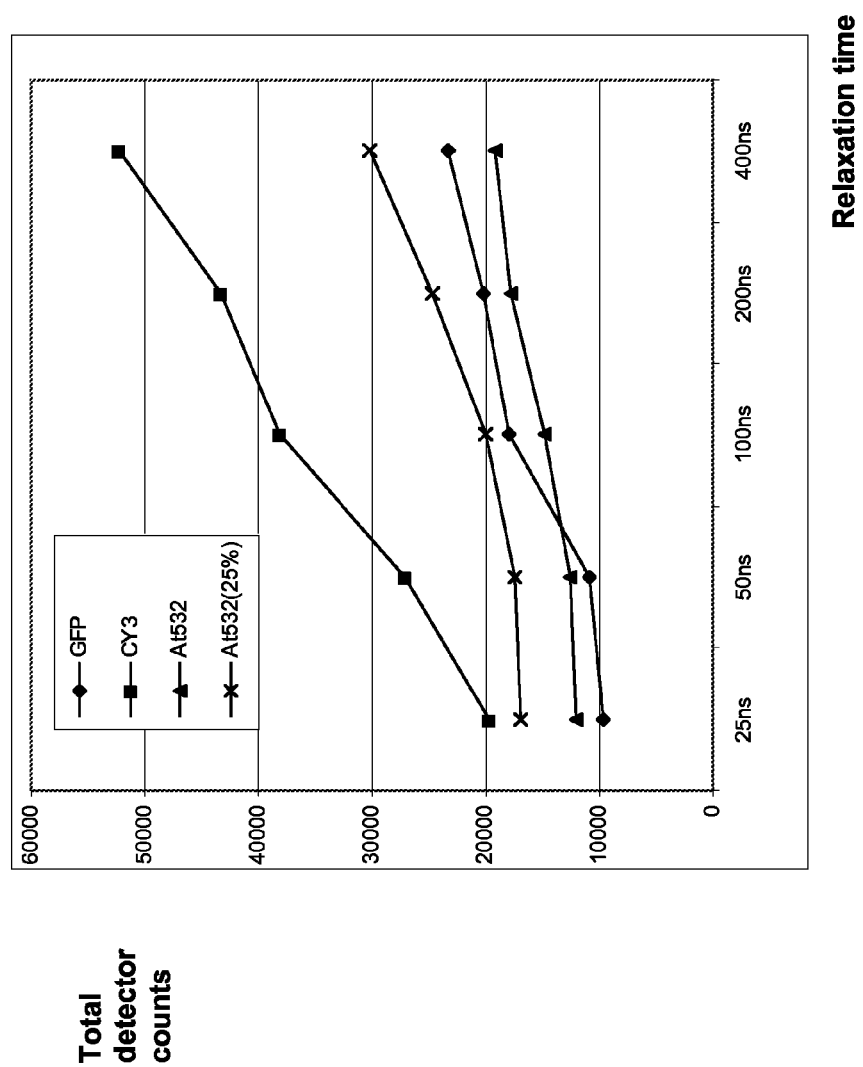

FIGS. 5 and 6 are plots of experimental data for a selection of dyes. Cell-free dyes spin-coated onto a microscope slide at low density were employed. In FIG. 5, fluorescent emission (represented as a count rate) is plotted against excitation s intensity for a fixed amount of continuous wave (CW) excitation (applied in wide field mode). "DiI" denotes the dye dioctadecyl-3,3,3',3'-tetramethylindocarbocyanine perchlorate $DiIC_{18}(3)$. FIG. 6 is a plot of fluorescent emission as a function of relaxation time. An improvement in photo-emission as the relaxation time is increased is apparent.

In some embodiments, combining intensity reduction and increases in inter-pulse relaxation time can maximise the total number of emitted photons. In a given experiment, it may be preferable to modulate one of these two parameters having regard to particular constraints such as detector noise, the scanning mechanism selected, or experimental kinetics, for example.

Characteristics of the excitation procedure selected (such as excitation pulse duration, power level and pulse repetition rate) may be established having regard to other conditions which affect photobleaching, such as the sample concentration, its temperature, and/or the presence of particular species in the sample, notably molecular oxygen, for example. Characteristics of the microscope system itself may also be taken into account, such as the level of detection noise, the maximum power output of the excitation energy source, the capabilities of its shutter arrangement and/or scanning mechanism, and so on.

An excitation regime may be selected according to the specific excitation and/or emission waveband being imaged in order to facilitate multi-channel imaging.

The present teachings may also be implemented so as to maximise the rate at which fluorescent labels in a sample are photobleached. In an embodiment, this can be achieved by controlling or setting the characteristics of the excitation procedure (such as excitation pulse duration, power level, and pulse repetition rates) so as to maximise the total photon emission by decreasing the overall rate at which the fluorescent labels can relax from excited to ground state for a given experiment and experimental conditions, whilst increasing the rate at which the fluorescent labels will move from the dark (or triplet) state to bleached state. These techniques are particularly applicable to FRAP experiments, for example.

Furthermore, the techniques may also provide a way of enhancing the effectiveness and efficiency of approaches such as PALM and STORM by selecting an appropriate excitation regime by which the desired level of bleaching (or photo-activation) may be obtained.

Figure 7:
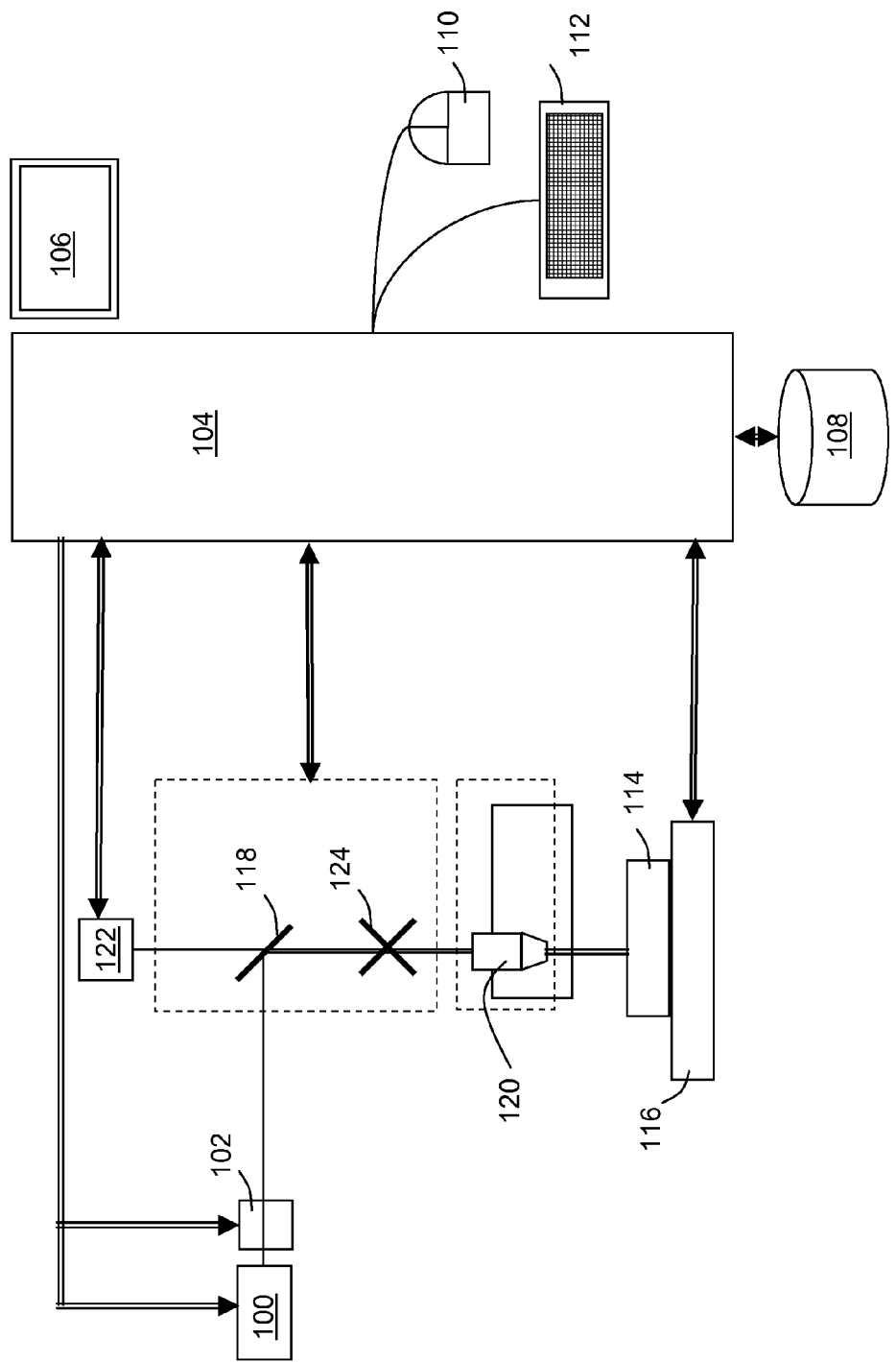
FIG. 7 is a schematic representation of a fluorescence microscope system according to an embodiment of the present invention.

A fluorescence microscope embodying an apparatus in accordance with the invention is shown schematically in FIG. 7.

Excitation energy is provided by an excitation energy source 100. The source may be in the form of one or more lasers, solid state lasers, diode pumped solid state lasers or LEDs. Alternatively, it may be a polychromatic source such as a white light source, lamp, or photonic crystal configured with a wavelength selection method. It may be polarised or unpolarised.

Energy from the source is transmitted towards a shutter mechanism 102. This facilitates interruption of the energy from the source for a controllable period of time and at high speed. In practice, this may be implemented as part of the source, for example in its power control, or it may be a separate element placed in the energy path. For example, it may be a solid state device or a mechanical device. It is preferably electrically controllable.

The excitation energy source and the shutter mechanism together form an agile source able to provide an excitation regime under the control of a computer 104. A display 106 and memory 108 are provided in association with the computer. In the illustrated embodiment, a mouse 110 and keyboard 112 provide input devices for operation by a user. An energy beam emerging from the shutter mechanism is directed towards a sample 114 mounted in a sample holder unit 116. The beam is deflected by a dichroic mirror arrangement 118 towards an objective lens 120. It may also pass through one or more filters (not shown) before impinging on the sample.

Light emanating from the sample is passed by the dichroic mirror arrangement and is incident on a detector 122. The detector 122 and sample holder unit 116 are operated under the control of the computer 104.

Optionally, a scanning mechanism 124 may be included in the beam path to and from the sample. Alternatively, this mechanism may be omitted and the sample exposed to an energy beam in a wide field configuration.

The scanning mechanism 124 may be operated under control of the computer to guide a single spot to various points on the sample using an aperture and one or more mirrors controllable along orthogonal X and/or Y axes. The aperture may be shaped to provide a spot which is circular or rectangular (square or slit shaped).

In some cases, a plurality of spots may be scanned simultaneously over different portions of the sample. To this end, the scanning arrangement may include one or more rotating disks, a linearly scanning grid, an array of individually controllable optical elements such as mirrors elements, or another suitable configuration. The scanning mechanism is preferably electrically controllable in terms of the location of the regions scanned, its scanning speed and dwell time.

In a further variation, an illuminated array of pinholes may be emulated by an array of individually controllable light sources, such as LEDs for example.

Pulsing of the excitation beam may be combined with the scanning mechanism so that the shuttering period of the excitation beam is used to move to the next point in the sample by combining the control of the source, shutter and scanning.

The sample 114 may be a biological, chemical or biochemical sample, such as a cell, array of cells, tissue, cell isolate, biochemical assembly, or a distribution of molecules in a medium. The sample includes one or more fluorescent molecules provided to label molecules of interest. The sample holder unit 116 may be a slide, dish, well, multi-well plate on a fixed or mobile platform. It may be operable to transport the sample in X, Y and Z directions.

The detector 122 has one or more light-sensitive elements. It may include one or more photomultiplier tubes, a linear or rectangular array of photodetectors, or a CCD array.

A program installed on the computer 104 or implemented in hardware governs control signals transmitted to elements of the microscope so as to control the excitation procedure.

The detector 122 may include a gated intensifier. In this event, the excitation procedure may be configured such that each excitation pulse comprises a set of very short (100 fs to 10 ns) pulses which trigger the gated intensifier in order to facilitate lifetime imaging (FLIM) and discrimination of different dye lifetimes.

In some embodiments, the scanning mechanism 124 may include a spinning disk which has a set of pinholes arranged in a repeating pattern therein. In such an arrangement, the power level will be set by the power of the excitation source and the associated optics; the excitation pulse duration will be a function of the size of the pinholes, the magnifying optics, and the rotational speed of the disk; the relaxation time will depend on the arrangement of pinholes on the disk (and thus how many degrees of rotation separate the pinholes), and the rotational speed of the disk; and the pulse repeat period is in turn determined by the relaxation time and the pulse duration. The commercially available disk systems offer rotational speeds of 1800 rpm, 5000 rpm or 10,000 rpm according to the model selected.

As noted above, a confocal fluorescence microscope is disclosed herein which includes a spinning disk, wherein the rotational speed of the disk is variable under the control of a processing arrangement of the microscope. Preferably, the rotational speed is under computer control with feedback as to the speed attained, and a rapid response to a commanded speed. The microscope may be configured to switch between different excitation regimes by changing the rotational speed. Samples including more than one fluorescent label of interest may thereby be imaged by switching between excitation regimes suitable for each label and imaging each label in turn. Excitation and/or emission filters may be switched as appropriate for each label. The processing arrangement may determine suitable intensity and relaxation time operating points for each type of label.

In existing spinning disk mechanisms, the pinhole arrangement is selected so as to optimise the spacing and thereby reduce optical crosstalk (for a given magnification). In preferred implementations of the present techniques, a number of different pinhole arrangements may be provided by a mechanism for selection. Varying pinhole sizes and separations will offer different pulse durations and relaxation times. For example, imaging a particular sample may benefit from extending the pulse duration so that the excitation intensity can be reduced, whilst keeping the relaxation time constant, even if this results in some optical crosstalk and loss of image quality.

Different pinhole arrangements may be made available at different radial locations on the disk and brought into use by a linear radial movement of the excitation energy beam relative to the disk.

Figure 8:
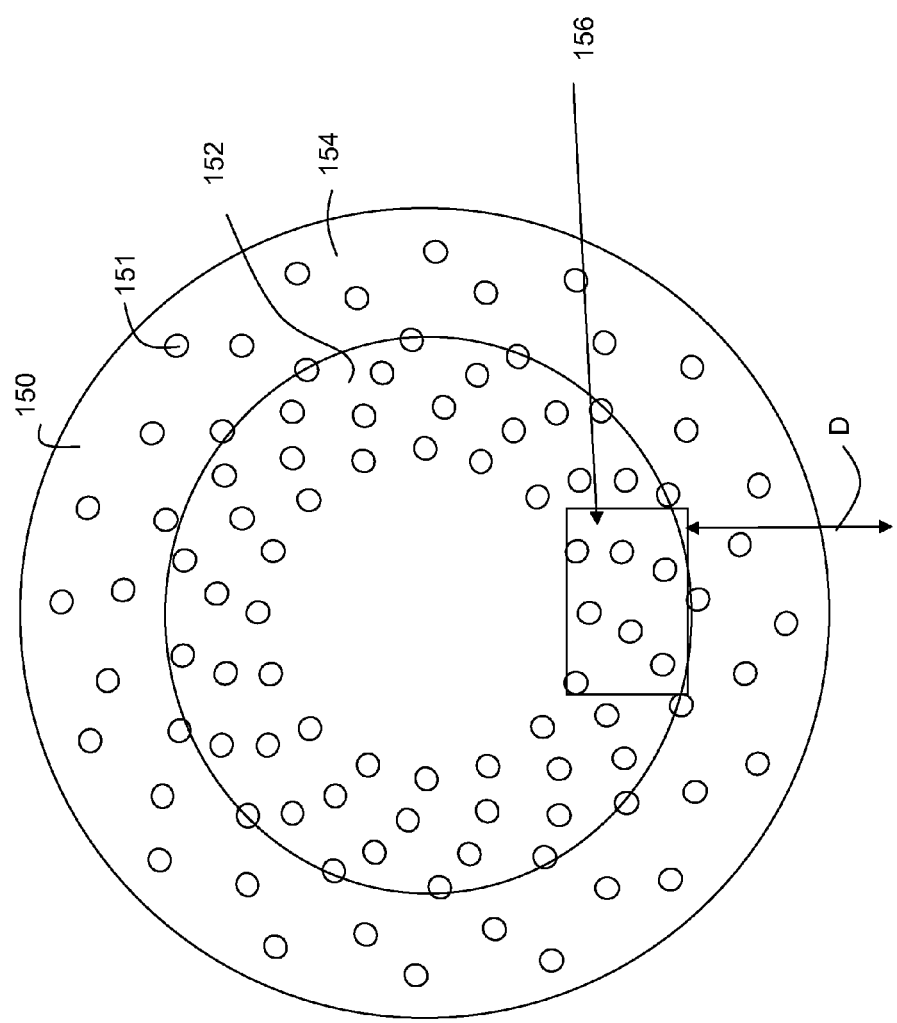
FIGS. 8 and 9 shows spinning disk configurations according to the two embodiments of the invention.

FIG. 8 illustrates an embodiment of a disk 150 for use in a spinning disk scanning mechanism. It has a relatively dense layout of pinholes 151 over an inner portion 152 surrounded by a more sparse layout over an outer portion 154. Rectangular region 156 represents an area irradiated by an energy beam which can be moved radially outwards in direction D into the outer portion to change the excitation regime.

Figure 9:
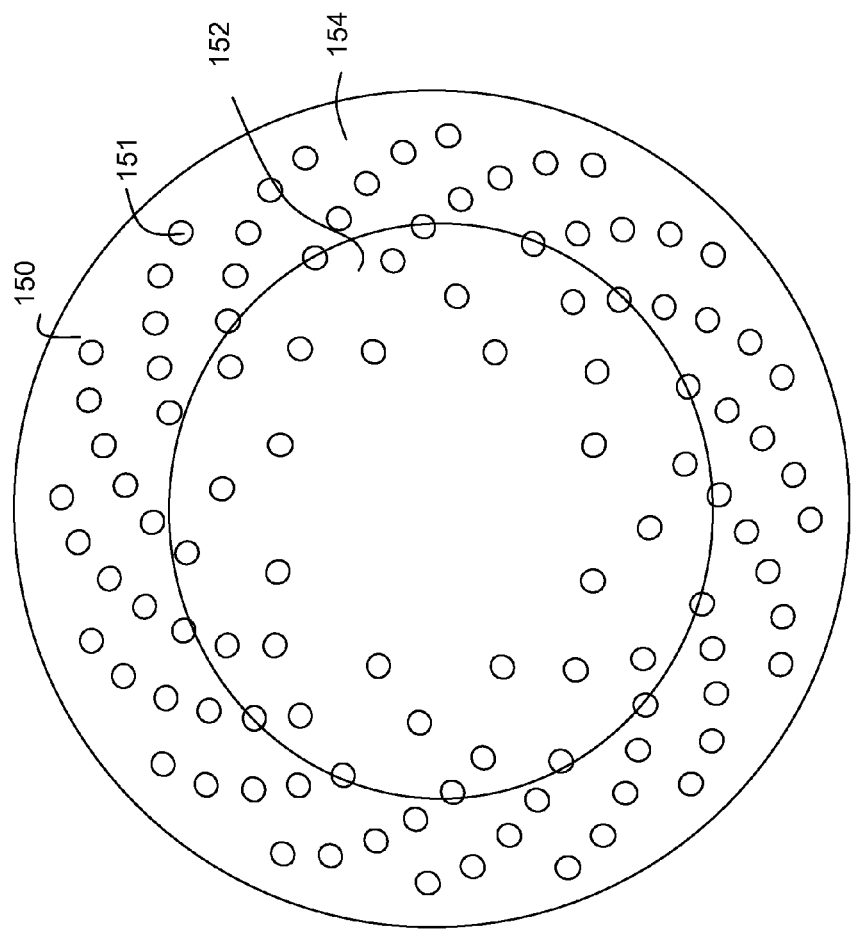

FIG. 9 shows a disk configuration that is the reverse of the FIG. 8 embodiment. In this case, the pinholes are more sparse in the inner portion 152 of the disk.

In addition to the spinning disk implementation, a number of alternative scanning mechanisms are known, involving translating arrays or translating bands on which arrangements of pinholes have been defined. In some cases the pinholes may be replaced by slits to increase the throughput of light, albeit with some loss of confocality. As in the modified spinning disk arrangement described above, in each of these implementations, different regions may be formed with different pinhole arrangements.

Figure 10:
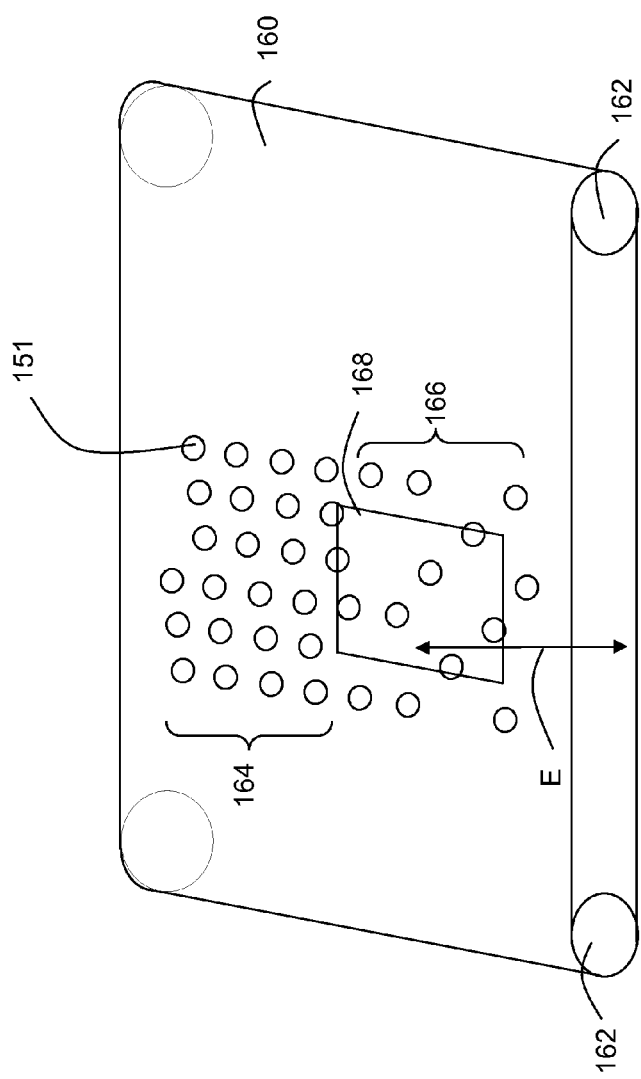
FIG. 10 is a perspective view of a translating band according to a further embodiment of the invention.

In a linear band, the scanning movement is a translation along one axis and different pinhole arrangements may be made available in different regions across the band and brought into use by a linear movement along an axis orthogonal to the scanning movement. A schematic representation of a translating band 160 illustrating this approach is shown in FIG. 10. The band passes around a pair of rollers 162. A more dense distribution of pinholes 151 is formed in an upper portion 164 of the band (as viewed in FIG. 10), relative to lower portion 166. Area 168 indicates a region irradiated by an energy beam in use of this scanning arrangement which is moveable in a direction E relative to the band. The pinholes are only shown in a localised area of the band for the purposes of illustration. In practice the pinholes will extend over the full length of the band.

Figure 11:
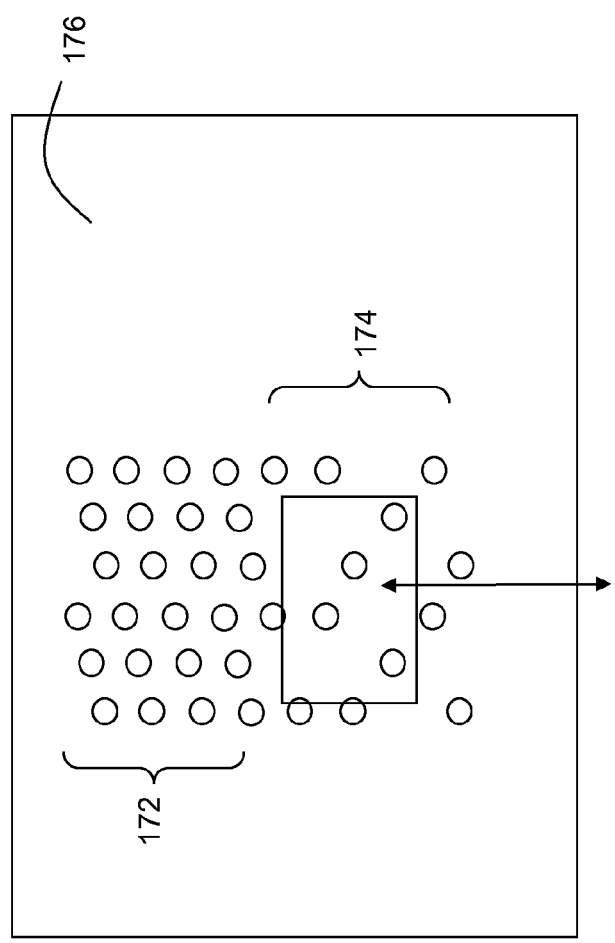
FIG. 11 shows a translating array of pinholes according to another embodiment of the invention.

In a translating array, the movement is typically an oscillating one in X and Y. Here again (as illustrated in FIG. 11), different regions 172,174 of the array plane 176 may be formed with different pinhole arrangements.

According to a further aspect of the present disclosure, it is possible to modulate the power of the excitation beam during the excitation pulse. This may be employed to provide a higher power for a shorter time to either bleach a sample, or extend the average relaxation time as a smaller population will be excited by the higher powered beam, for example. A larger pinhole size may be preferable in this case.

Figure 12:
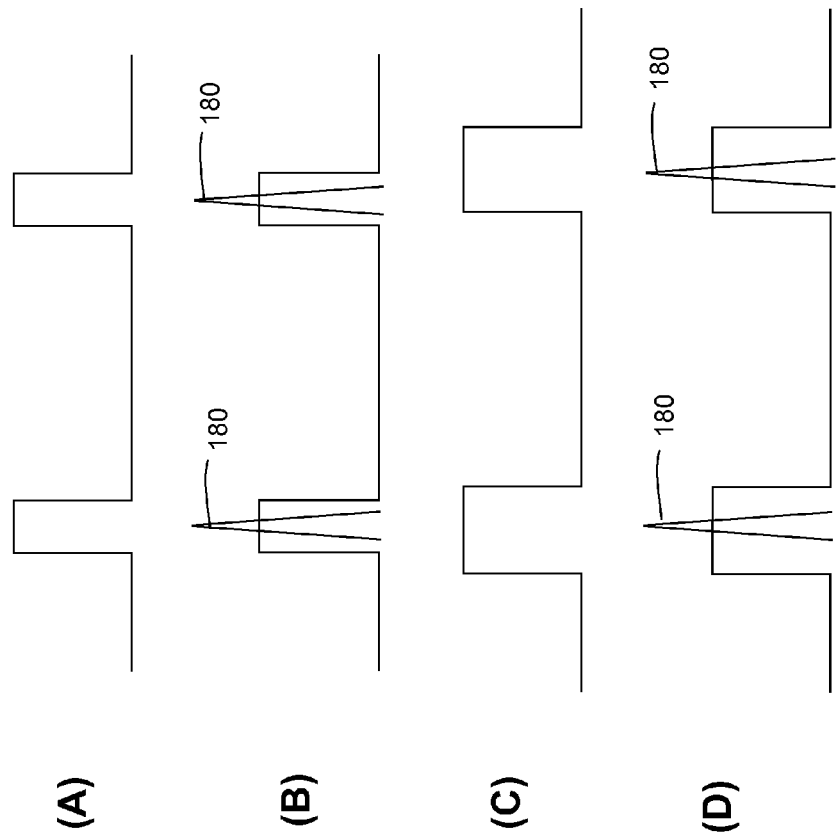
FIG. 12 shows a series of pulse trains to illustrate pulse profiles modulation in accordance with a still further embodiment of the invention.

FIG. 12 shows four plots against time (A) to (D). Each plot includes a continuous line which has brief "on-times" representing when a pinhole is present in the light path from the light source to a given point on a sample (the "pinhole aperture time"), with a longer "relaxation time" between successive on-times. In the case of the lower two plots (C) and (D), the scan speed is the same as for (A) and (B), but the pinhole apertures are larger and so the pinhole aperture time is longer. Excitation light pulses 180 have been superimposed on photos (B) and (D). It can be seen that if the excitation beam power can be modulated, there will be freedom to alter the pulse timing and/or profile within the pinhole aperture time available, with the longer aperture time of plot (D) giving greater scope for timing variation than that of plot (B).

In known spinning disk arrangements, the excitation received by a fluorescent moiety is determined by the mathematical product of the power level and the pulse duration, which is in turn dependent on the size of the pinhole. As is apparent from the non-linear relationship between photobleaching and intensity (see FIG. 2), this restricts control for reduced bleaching. The ability to modulate the excitation beam during the excitation pulse would provide a greater degree of versatility.

According to a further aspect, the profile of the light beam emerging from a pinhole may be modulated. More particularly, it may be altered such that its intensity is substantially uniform across the profile.

In known scanning mechanisms the beam typically has a profile resembling that of a Gaussian distribution, being initially low in intensity, then increasing before peaking and falling at a rate substantially similar to the aforementioned rate of increase.

In present embodiments, the magnitude of the peak may be attenuated to distribute the beam intensity more evenly over the beam width. Thus, the total excitation energy may remain substantially the same, that is the area under a plot of the beam intensity profile may be essentially unchanged. However, the effect of the modified optical arrangement is to reduce the peak intensity, distributing the excitation energy more uniformly across the beam profile than would be the case for a substantially Gaussian form of profile.

Figure 13:
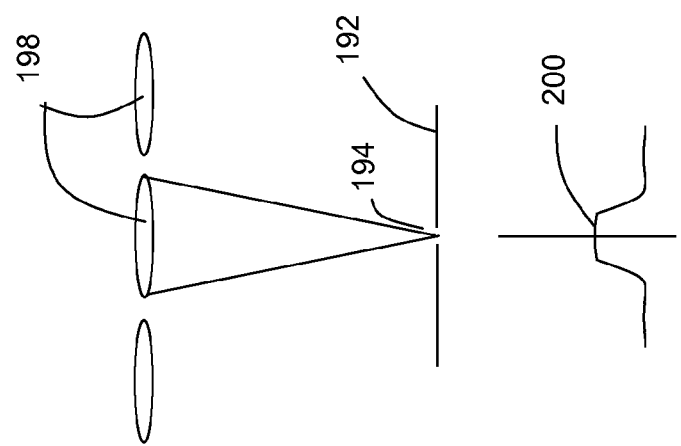
FIGS. 13 and 14 illustrate beam profile formation in a known scanning mechanism and a mechanism embodying the present invention, respectively.

A beam profile flattening or so-called "top-hatting" optical configuration may be employed. In certain example embodiments, a Fresnel lens approach may be adopted. In some known scanning arrangements, the pinhole arrangement uses a microlens array in the upper disk. FIG. 13 shows such a configuration. Microlenses 190 are mounted in an upper disk (not shown). A light beam incident on these lenses is brought to a focus in the plane of a lower disk 192 which includes an array of pinholes 194. This results in a beam profile 196 which has a pronounced central peak.

Figure 14:
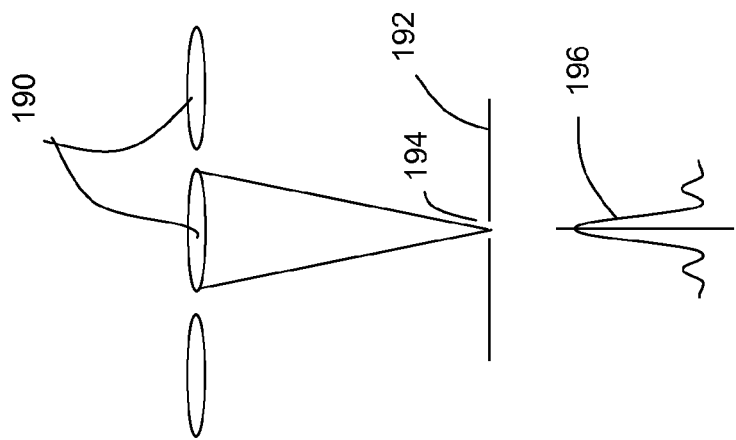

In embodiments of the present concept, the design of each microlens is modified so as to flatten the beam profile. Modulation of the beam profile can achieve a reduction in bleaching, although this may be at some cost in excitation light intensity. FIG. 14 shows a configuration similar to that of FIG. 13, except that microlenses 198 have been modified by inclusion of a beam profile flattening element so that a flattened beam profile 200 is created. The bleaching potential of the flattened beam cross-sectional profile 200 is reduced relative to that of profile 196 which exhibits a higher peak intensity.

References

G. M. Hagen, W. Caarls, M. Thomas, A. Hill, K. A. Lidke, B. Rieger, C. Fritsch, B. van Geest, T. M. Jovin, and D. J. Arndt-Jovin, 2007, "Biological applications of an LCoS-based programmable array microscope (PAM)", Proc. SPIE 6441, 64410S.

V. Poher, H. X. Zhang, G. T. Kennedy, C. Griffin, S. Oddos, E. Gu, D. S. Elson, J. M. Girkin, P. M. W. French, M. D. Dawson and M. A. A. Neil, 2007, "Optical sectioning microscopes with no moving parts using a micro-stripe array light emitting diode", Optics Express, Vol. 15, Issue 18, pp. 11196-11206.

N. C. Shaner, P. A. Steinbach and R. Y. Tsien, 2005, "A guide to choosing fluorescent proteins", Nature Methods 2(12), Dec, pp. 905-909.

R. A. Hoebe, C. H. van Oven, T. W. J. Gadella, P. B. Dhonukshe, C. J. F. van Noorden and E. M. M. Manders, 2007, "Controlled light-exposure microscopy reduces photobleaching and phototoxicity in fluorescence live-cell imaging", Nature Biotechnology, Jan 21.

I. Rasnik, S. A. McKinney and T. Ha, 2006, "Non-blinking and long-lasting single-molecule fluorescence imaging", Nature Methods 3(12), pp. 891-893.

E. Betzig et al, 2006, "Imaging Intracellular Fluorescent Proteins at Nanometer Resolution", Science, 15 Sep. 2006, Vol. 313. no 5793, pp. 1642-1645.

M. J. Rust, M. Bates and X. Zhuang, 2006, "Sub-diffraction-limit imaging by stochastic optical reconstruction microscopy (STORM)", Nature Methods—3, 793-796.

The invention claimed is:

1. A method of operating fluorescence microscopy apparatus to analyse a sample, the apparatus including input, processing, sample irradiating and detection arrangements, the method comprising the steps of:
   (a) using the input arrangement to transfer to the processing arrangement a set of parameters that relate to an experiment to be conducted using the apparatus and include at least one label parameter that identifies an inherent characteristic of a fluorescent label present in the sample and a rate parameter that identifies a rate of photobleaching of the fluorescent label desired during the experiment;
   (b) causing the processing arrangement to use the inputted parameters and take into account the identified characteristic of the fluorescent label while determining, prior to the initiation of irradiation, an excitation procedure to be carried out during the experiment to achieve the desired rate of photobleaching of the fluorescent label present in the sample during the experiment;
   (c) using the sample irradiating arrangement to irradiate at least part of the sample in accordance with the excitation procedure and substantially achieve the identified rate of photobleaching of the fluorescent label desired during the experiment; and
   (d) detecting with the detection arrangement fluorescent radiation emitted by the labels in the sample in response to the excitation energy.

2. A method of claim 1, wherein the parameters include at least one of: the excitation procedure duration, the sampling rate of the detection arrangement, the location and dimensions of a part of the sample to be irradiated, the relative speed of a process of interest in the sample, the rate at which a beam of irradiation energy is scanned over the sample, and the intensity of the excitation energy.

3. A method of claim 1, wherein the parameters include at least one of the following sample parameters: temperature, the concentration of a fluorescent label in the sample, oxygen concentration, the presence of an oxygen scavenger system, and a parameter relating to an oxygen scavenger system present in the sample.

4. A method of claim 1, wherein the at least one label parameter includes at least one of the following: peak excitation wavelength, peak emission wavelength, fluorescence lifetime, triplet state decay lifetime, and a parameter identifying a particular fluorescent label.

5. A method of claim 1, wherein the excitation procedure is determined by the processing arrangement in step (b) having regard to at least one of the following characteristics of the apparatus: the level of detector background noise, the maximum power output of the sample irradiating arrangement, the capabilities of a shutter arrangement associated with a source of irradiation energy, and the capabilities of a sample scanning mechanism.

6. A method of claim 1, wherein the processing arrangement determines at least one of the following aspects of the excitation procedure in step (b): the excitation pulse duration, the pulse intensity versus time profile, the pulse repetition rate, the time interval between groups of pulses, and the rotational speed of a spinning disk in a sample scanning mechanism.

7. A method of claim 6, wherein the sample irradiating arrangement is operable to vary the power of a beam of excitation energy generated during an excitation pulse so as to control the pulse intensity versus time profile.

8. A method of claim 1, wherein the sample includes a plurality of different fluorescent labels, and the processing arrangement determines a respective excitation procedure to be carried out during the experiment for at least two different fluorescent labels.

9. A method of claim 1, wherein the excitation procedure is determined by the processing arrangement in step (b) having regard to an electronically accessible library of test data relating to the fluorescence characteristics of a plurality of fluorescent labels.

10. Fluorescence microscopy apparatus for analysing a sample according to a method of claim 1, comprising:
   (i) an input arrangement for inputting parameters relating to an experiment to be conducted, which parameters include at least one label parameter identifying an inherent characteristic of a fluorescent label present in the sample and a rate parameter identifying a rate of photobleaching of the fluorescent label desired during the experiment;

(ii) a processing arrangement configured to determine an excitation procedure to be carried out during the experiment having regard to the inputted parameters, the procedure being determined with a view to achieving the desired rate of photobleaching of emissions from the fluorescent label present in the sample during the experiment as identified by the rate parameter and with reference to the characteristic of the fluorescent label identified by the at least one label parameter;

(iii) a sample irradiating arrangement for irradiating at least part of the sample in accordance with the excitation procedure; and (iv) a detection arrangement for detecting fluorescent radiation emitted by labels in the sample in response to the excitation energy.

11. Apparatus of claim 10, including an optical arrangement in the light path from an excitation energy source to a sample which acts to adjust the intensity profile of the light beam across its width so as to be more evenly distributed than a Gaussian profile.

12. Apparatus of claim 11, wherein the optical arrangement comprises a Fresnel lens.

13. Apparatus of claim 11 in the form of confocal fluorescence microscopy apparatus and including a spinning disk having an array of microlenses therein, each of which acts to adjust the intensity profile of the respective light beam across its width so as to be more evenly distributed than a Gaussian profile.

14. Apparatus of claim 10 in the form of confocal fluorescence microscopy apparatus, wherein the apparatus includes a multiple point scanning mechanism having a mask arrangement which defines at least two regions having different respective aperture configurations, the apparatus being configured to select one of the regions for use in a particular excitation procedure.

15. Apparatus of claim 14, wherein the mask arrangement comprises one of: a spinning disk, a linear band, and a translating array.

16. Apparatus of claim 14, wherein the regions differ with respect to at least one of: the dimensions of the apertures, and the spacing between the apertures.

17. Apparatus of claim 10 in the form of confocal fluorescence microscopy apparatus comprising an optical arrangement in the light path from an excitation energy source to a sample which acts to adjust the intensity profile of the light beam across its width so as to be more evenly distributed than a Gaussian profile.

18. Apparatus of claim 17, wherein the optical arrangement comprises a Fresnel lens.

19. Apparatus of claim 17 including a spinning disk having an array of microlenses therein, each of which acts to adjust the intensity profile of the respective light beam across its width so as to be more evenly distributed than a Gaussian profile.

20. Apparatus of claim 17, wherein the apparatus includes a multiple point scanning mechanism having a mask arrangement which defines at least two regions having different respective aperture configurations, the apparatus being configured to select one of the regions for use in a particular excitation procedure.

21. Apparatus of claim 10 in the form of confocal fluorescence microscopy apparatus including a spinning disk, wherein the rotational speed of the disk is variable under the control of a processing arrangement of the apparatus.

22. Apparatus of claim 21, wherein the apparatus includes a multiple point scanning mechanism having a mask arrangement which defines at least two regions having different respective aperture configurations, the apparatus being configured to select one of the regions for use in a particular excitation procedure.

* * * * *